United States Patent [19]

Love et al.

[11] Patent Number: 5,049,675

[45] Date of Patent: Sep. 17, 1991

[54] SOLVENT-FREE PROCESS FOR THE PREPARATION OF ((PYRIDINYLOXY)PHENOXY) PROPIONATE DERIVATIVES

[75] Inventors: Jim Love; Charles B. Grant; Sterling Gatling, all of Midland, Mich.

[73] Assignee: DowElanco, Indianapolis, Ind.

[21] Appl. No.: 471,347

[22] Filed: Jan. 29, 1990

[51] Int. Cl.$^5$ ............. C07D 213/64; C07D 213/643; C07D 213/78
[52] U.S. Cl. .................................... 546/302; 546/301; 546/303
[58] Field of Search ........................ 546/301, 302, 303

[56] References Cited

U.S. PATENT DOCUMENTS 4,046,553  9/1977  Takahashi et al. ..................... 71/94
4,565,568  1/1986  Johnston et al. ....................... 71/94
4,753,673  6/1988  Johnston et al. ....................... 71/94

Primary Examiner—Alan L. Rotman
Attorney, Agent, or Firm—Ronald G. Brookens; Craig E. Mixan

[57] ABSTRACT

A solvent-free process for the preparation of herbicidal 2-(4-(pyridinyl-2-oxy)phenoxy)propionate esters is disclosed. The process involves the coupling of a 2-fluoropyridine and an ester of 2-(4-hydroxyphenoxy)-propionic acid in the presence of an anhydrous base and in the absence of an added solvent.

10 Claims, No Drawings

SOLVENT-FREE PROCESS FOR THE PREPARATION OF ((PYRIDINYLOXY)PHENOXY) PROPIONATE DERIVATIVES

FIELD OF THE INVENTION

The present invention relates to the preparation of ((pyridinyloxy)phenoxy)propionate derivatives in the absence of an added solvent. More particularly, the present invention is directed to a solvent-free process for the preparation of 2-(4-(pyridinyl-2-oxy)phenoxy)-propionate esters from 2-fluoropyridines and 2-(4-hydroxyphenoxy)propionate esters in the presence of an anhydrous base.

BACKGROUND OF THE INVENTION

The herbicidal activity of 2-(4-(pyridinyl-2-oxy)-phenoxy)propionic acids and derivatives thereof is well known in the art; see, for example, U.S. Pat. Nos. 4,046,553, 4,565,568 and 4,753,673. Furthermore, U.S. Pat. No. 4,531,969, for example, teaches that the R-enantiomers of these propionic acids exhibit enhanced herbicidal activity over the corresponding racemates. These same references teach that 2-(4-(pyridinyl-2-oxy)phenoxy)propionic acids and derivatives thereof can be conveniently prepared by reacting substituted 2-halopyridines with 2-(4-hydroxyphenoxy)propionic acid or derivatives thereof under alkaline conditions. The optically active R-enantiomers are similarly prepared by using optically active R-2-(4-hydroxyphenoxy)propionate derivatives. The coupling reaction is generally conducted in a polar aprotic organic solvent such, as, for example, acetonitrile, dimethyl sulfoxide (DMSO), dimethyl formamide (DMF) or N-methylpyrrolidinone (NMP).

Although this process generally achieves good yields, it has the disadvantage of using organic solvents which must be separated from the reaction mixture. The separation of the organic solvents from the reaction mixture after formation of the product can require multiple steps and high energy expenditures. After separation, the organic solvents require either waste disposal and/or recycling which often implies elaborate or expensive apparatus. Thus it would be highly desirable to have a process for preparing ((pyridinyloxy)phenoxy)-propionate derivatives which eliminates the need of using any solvent.

SUMMARY OF THE INVENTION

The present invention is directed to a process for preparing a 2-(4-(pyridinyl-2-oxy)phenoxy)propionate ester of the formula:

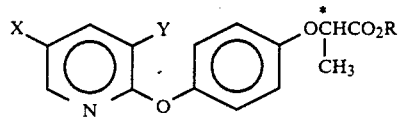

wherein
X represents Cl, Br, I or CF$_3$,
Y represents H, F or Cl, provided that when Y is H, X is CF$_3$, and
R represents lower alkyl, which comprises contacting a 2-fluoropyridine of the formula

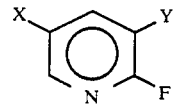

wherein
X and Y are as previously defined, with about an equimolar amount of an (hydroxyphenoxy)propionate ester of the formula

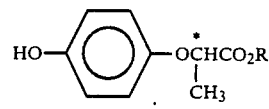

wherein
R is as previously defined, in the presence of an anhydrous base and in the absence of an added solvent; and recovering said 2-(4-(pyridinyl-2-oxy)phenoxy)propionate ester. The "*" denotes a chiral carbon atom. Compounds with such chiral carbon atoms can exist as enantiomers, i.e., mirror image isomers that are not superimposable.

As to the substituents X and Y, X is preferably CF$_3$ and Y is preferably Cl or F. As to the ester, R is preferably a branched- or straight-chain alkyl group of from 1 to 4 carbon atoms. The R-enantiomers are most preferred. The preferred anhydrous base is K$_2$CO$_3$, preferably with a particle size between about 100 and about 350 microns.

In another aspect of the present invention, the reaction can be optionally conducted in the presence of a phase-transfer catalyst. Preferably, the phase-transfer catalyst is a quaternary ammonium salt, most preferably a tetraalkyl ammonium halide.

The present invention has the advantage of simplifying the process for the preparation of 2-(4-(pyridinyl-2-oxy)phenoxy)propionate esters by eliminating the need for solvent recovery and recycling operations. By eliminating the solvent, a savings in raw material cost and an effective increase in reactor capacity are achieved. Furthermore, when preparing optically active R-enantiomers, the present process provides a reduction in the amount of racemization experienced in comparison to those reactions conducted, for example, in DMSO.

DETAILED DESCRIPTION OF THE INVENTION

The term "lower alkyl", as used herein, is meant to designate straight, branched or cyclic, saturated or unsaturated alkyl groups of up to and including 8 carbon atoms, such as, for example, methyl, ethyl, propyl, isopropyl, butyl, iso-butyl, sec-butyl, hexyl, ethylhexyl, octyl, allyl, cyclohexyl and the like.

The 2-fluoropyridine starting materials are known compounds and can be prepared by known methods: see, for example, U.S. Pat. Nos. 4,625,035, 4,745,193 and 4,851,539. Similarly, the 2-(4-hydroxyphenoxy)propionate esters are known compounds and can be prepared by conventional synthetic procedures.

The 2-fluoropyridines can be contacted with the 2-(4-hydroxyphenoxy)propionate ester in about equimolar ratios ranging from 0.9:1 to about 1.5:1, more preferably from about 1:1 to about 1.15:1 (propionate ester:fluoropyridine).

The anhydrous base is used to prepare and maintain the (hydroxyphenoxy)propionate ester in its reactive anionio or phenolate form during its reaction with the fluoropyridine, while avoiding the undesirable hydrolysis of the ester funotionality. In addition, the anhydrous base should be unreactive with the fluoropyridine so as not to compete with the desired coupling reaction, particularly if an excess of the base be employed. Any anhydrous base that meets these criterion can be employed.

The alkali metal (Li, Na, K) carbonates are among the preferred anhydrous bases with potassium carbonate being most preferred.

The amount of anhydrous base employed in the present process can range from about 1 to about 5 moles of base and higher per mole of (hydroxyphenoxy)propionate ester. Generally from about 1.1 to about 1.5 moles of base per mole of (hydroxyphenoxy)propionate ester is preferred.

The alkali metal carbonates are granular materials and the rate of the coupling reaction has been found to be dependent on particle size. In general, the smaller the particle size, the faster the reaction is completed. However, if the particle size becomes too small, stirring becomes difficult and ester hydrolysis increases. Particle sizes from 75 to 500 microns have been found to give acceptable rates without unacceptable levels of ester hydrolysis. Particles in the range of 100 to 350 microns are preferred.

The contacting of the 2-fluoropyridine and the 2-(4-hydroxyphenoxy)propionate ester is carried out at temperatures ranging from about 55° to about 100° C., preferably from about 75° to 90° C. Higher temperatures tend to increase the amount of ester hydrolysis. The contacting is normally carried out at ambient pressures with stirring or other means of agitation.

In many instances, the order of addition of the reactants is inconsequential with respect to the final results. In the present process, however, it has been found to be beneficial to add the (hydroxyphenoxy)propionate ester to a mixture of the fluoropyridine and the base. By adding the (hydroxyphenoxy)propionate to a mixture of the fluoropyridine and base rather than by adding the fluoropyridine to a mixture of (hydroxyphenoxy)propionate and base, the amount of ester hydrolysis is reduced.

The contacting of the fluoropyridine and the (hydroxyphenoxy)propionate ester may optionally be conducted in the presence of a catalytic amount of phase transfer-catalyst. The term "phase-transfer catalyst" is intended to mean a material which catalyzes a reaction by the transfer of reactants from one phase to another. Phase-transfer catalysts suitable for use in the present process include quaternary ammonium and phosphonium salts. Suitable quaternary ammonium and phosphonium salts normally have an aggregate carbon content of at least 4 carbons to about 31 carbons, preferably from 4 carbons to about 16 carbons. The ammonium salts are currently preferred over the phosphonium salts due to cost and commercial availability. Suitable catalysts are, for example, the tetramethyl, benzyltriethyl, tetra-n-butyl and tri-n-butylmethyl ammonium salts, most preferably the tetramethyl and tetra-n-butyl ammonium salts.

The phase-transfer catalysts can be used in the process in small but catalytic amounts. For example, amounts from about 0.1 to about 20 mole percent, based on the reactants, are suitable but amounts of from about 0.1 to about 10 mole percent are generally preferred. Amounts from about 1 to about 6 mole percent are most preferred. The use of a phase-transfer catalyst results in a reduction of ester hydrolysis. Thus, when a phase-transfer catalyst is employed, the order of addition of the reactants is of significantly less consequence.

The coupling reaction can be carried out by vigorously mixing the 2-fluoropyridine, the 2-(4-hydroxyphenoxy)propionate ester, the anhydrous base and optionally a phase-transfer catalyst and by heating the mixture. If a phase transfer-catalyst is used, the order of mixing the components is not critical. Without a phase-transfer catalyst, it is beneficial to add the (hydroxyphenoxy)propionate ester to a mixture of anhydrous base and fluoropyridine. Because no solvent is added to the reaction mixture, it is desirable that the requisite reaction temperature be maintained above the melting point of the crude product.

After the reaction is complete, usually in about 1 to about 24 hours (hr), the product 2-(4-(pyridinyl-2-oxy)-phenoxy)propionate ester is recovered by conventional procedures. For example, any phase-transfer catalyst, residual base or inorganic salt produced during the reaction are typically removed by a simple aqueous wash, ion-exchange treatment, filtration, aqueous extraction or the like. The product can be recovered and purified by routine techniques such as phase separation, extraction, distillation or recrystallization.

The following examples illustrate the present invention in a manner by which it can be practiced but, as such, should not be construed as limitations upon the overall scope of the same.

Example 1

Preparation of Methyl 2-(4-((3-Chloro-5-trifluoromethyl-2-pyridinyl)oxy)-phenoxy)propionate

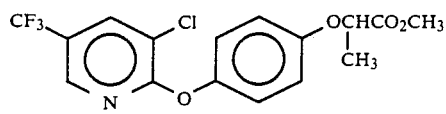

A 500 milliliter (mL) round-bottom flask was equipped with a mechanical paddle stirrer, an infrared heater connected to a thermocouple temperature controller and a drying tube. Methyl 2-(4-hydroxyphenoxy)propionate (103 grams (g): 0.5 moles) was introduced into the flask and heating was initiated to melt the solid. Stirring was begun and powdered anhydrous $Na_2CO_3$ (74.2 g: 0.70 moles) was added. After 5 minutes (min), the temperature was about 80° C. and the evolution of gas was proceeding. Tetra-n-butylammonium bromide (4.8 g: 0.015 moles) was added, followed by 100 g (0.5 moles) of 2-fluoro-3-chloro-5-trifluoromethylpyridine. After 70 min at 80° C, the temperature was raised to 90°. C. for an additional 230 min.

The reaction mixture was allowed to cool and 750 mL of water and 500 mL of $CH_2Cl_2$ were added. After mixing, the layers were separated. The aqueous layer was extracted with 50 mL of $CH_2Cl_2$ and the combined organic layers were washed with 50 mL of water. The solvent was evaporated under reduced pressure to give 200.4 g of viscous oil. After 3 days, the oil began to crystallize. The product was recrystallized from methanol and dried to give 148.3 g of white solid, mp 55.5°–56.5° C.

Example 2

Preparation of Methyl 2-(4-((3-Fluoro-5-trifluoromethyl-2-pyridinyl)oxy)-phenoxy)propionate

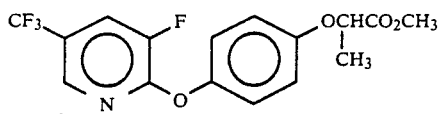

A 22 liter (L), 3-necked round-bottom flask with a bottom outlet was fitted with a mechanical stirrer, a condenser topped with a nitrogen inlet, and an addition funnel. Through the funnel, 6.546 kilograms (kg) (33.13 moles) of molten methyl 2-(4-hydroxyphenoxy)propionate, 6.571 kg (47.55 moles) of anhydrous $K_2CO_3$ and 319 g (0.99 moles) of tetra-n-butylammonium bromide were added to the reactor. Under constant agitation, the slurry was heated to 66° C. with a steam-water mixture controlled by a microprocessor and 6.026 kg (32.93 moles) of 2,3-difluoro-5-trifluoromethyl-pyridine was added over 15 min. The reaction mixture was heated for 13 hours (hr) at 70°–75° C. after which the product was washed 5 times using a total 37 L of hot water. The washed product was stripped of residual water using a rotary evaporator at 75° C. at a reduced pressure of 30 millimeters (mm) of mercury. A total 10.7 kg of product was collected having a purity of 97.9 percent.

Example 3

Preparation of Methyl R-2-(4-((3-Fluoro-5-trifluoromethyl-2-pyridinyl)-oxy)-phenoxy)propionate

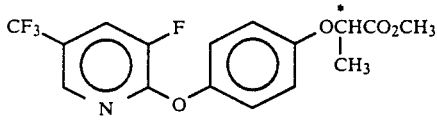

In a 1L flask equipped with a mechanical stirrer, condenser and addition funnel was charged 183 g (1.0 mole) of 2,3-difluoro-5-trifluoromethylpyridine and 193 g (1.4 moles) of anhydrous $K_2CO_3$ with a particle size range between 100 and 350 microns. Under constant agitation, the slurry was heated to 65° C. and 198 g (1.0 moles) of molten methyl R-2-(4-hydroxyphenoxy)propionate (R/S=93/7) was gradually added. The reaction mixture was heated for 16 hr at 85° C. and was subsequently washed 5 times using hot water. The washed product was stripped of residual water using a rotary evaporator at 75° C. and 30 mm Hg. Product having a purity of 99.2 percent and an R/S ratio of 93/7 (no racemization) was recovered in a 96 percent yield.

What is claimed is:

1. A process for the preparation of a 2-(4-(pyridinyl)-2-oxy)propionate ester of the formula

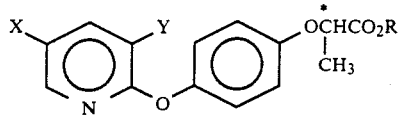

wherein
X represents Cl, Br, I or $CF_3$,
Y represents H, F, Cl, provided that when Y is H, X is $CF_3$, and
R represents lower alkyl, which comprises contacting a 2-fluoropyridine for the formula

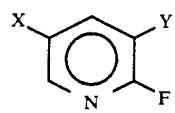

wherein X and Y are as previously defined, with about an equimolar amount of an (hydroxyphenoxy)-propionate ester of the formula

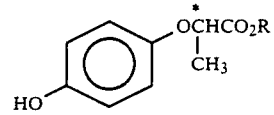

wherein R is as previously defined, in the presence of an anhydrous base and in the absence of an added solvent at a temperature from about 55° to about 100° C.; and recovering said 2-(4-(pyridinyl-2-oxy)phenoxy)propionate ester.

2. The process of claim 1 in which X is $CF_3$, and Y is F or Cl.

3. The process of claim 2 in which R is a branched- or straight-chain alkyl group of from 1 to 4 carbon atoms.

4. The process of claim 1 in which the optically active R-enantiomers are prepared.

5. The process of claim 1 in which the anhydrous base is an alkali metal carbonate.

6. The process of claim 5 in which the alkali metal carbonate is $K_2CO_3$.

7. The process of claim 5 in which the alkali metal carbonate has a particle size range from about 100 to about 350 microns.

8. The process of claim 1 in which the temperature is maintained between about 75° and about 90°.

9. The process of claim 1 in which a catalytic amount of a phase-transfer catalyst is employed.

10. The process of claim 9 in which the phase-transfer catalyst is a quaternary ammonium salt having an aggregate carbon content of at least 4 carbons to about 31 carbons.

* * * * *